(12) United States Patent
Venge et al.

(10) Patent No.: US 6,733,980 B1
(45) Date of Patent: *May 11, 2004

(54) DIAGNOSTIC METHOD FOR DETECTION OF MOLECULAR FORMS OF EOSINOPHILIC CATIONIC PROTEIN (ISO-ECPS)

(75) Inventors: Per Venge, Uppsala (SE); Christer Peterson, Storvreta (SE)

(73) Assignee: Pharmacia Diagnostics AB, Uppsala (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,667

(22) PCT Filed: Jun. 6, 1997

(86) PCT No.: PCT/SE97/00995

§ 371 (c)(1),
(2), (4) Date: Dec. 1, 1998

(87) PCT Pub. No.: WO97/46885

PCT Pub. Date: Dec. 11, 1997

(30) Foreign Application Priority Data

Jun. 6, 1996 (SE) .............................................. 9602234

(51) Int. Cl.[7] .......................... C12Q 1/68; G01N 33/53; G01N 33/567; G01N 33/555; G01N 33/537
(52) U.S. Cl. .................... 435/7.1; 424/1.41; 424/78.36; 424/85.1; 435/6; 435/7.2; 435/7.25; 435/7.92; 435/7.93; 435/7.94; 435/7.95; 435/334; 435/337; 435/343; 436/66; 436/69; 436/507; 436/517; 436/811; 530/350
(58) Field of Search .............................. 424/1.41, 78.36, 424/85.1; 435/6, 7.1, 7.2, 7.25, 7.92, 7.93, 7.94, 7.95, 334, 337, 343, 72; 530/350; 436/66, 69, 507, 517, 811

(56) References Cited

U.S. PATENT DOCUMENTS 5,567,590 A * 10/1996 Leung et al. .................. 435/72

FOREIGN PATENT DOCUMENTS

EP 535162 * 4/1993

OTHER PUBLICATIONS

Barker et al. 1989. eosinophil Cationic Protein cDNA. J. of Immu. 143(3):952–955.*

Olsson et al. 1986. Biochemical Properties of the Eosinophil Cationic Protein and Demonstration of its Biosynthesis In Vitro in Marrow cells From Patients With an Eosinophilia. blood. 67(2):498–503.*

(List continued on next page.)

Primary Examiner—Nita Minnifield
Assistant Examiner—JaNa Hines
(74) Attorney, Agent, or Firm—Sinsmore & Shohl LLP

(57) ABSTRACT

Diagnostic methods comprise measuring specifically the level of at least one iso-eosinophilic cationic protein (iso-ECP) in a sample from an individual to be diagnosed, and comparing the measured level of the iso-ECP with a predetermined level of the iso-ECP. The iso-ECP is cytotoxic and the cytotoxicity of the iso-ECP is not capable of neutralization by the monoclonal antibodies EG1 and EG2. Anti-iso-ECP antibody which may be used in the diagnostic methods specifically binds to a cytotoxic isoform of ECP having an epitope which is unique for the native form of the cytotoxic iso-ECP.

20 Claims, 11 Drawing Sheets

OTHER PUBLICATIONS

Makino et al. 1993. Eosinophils: Biological and clinical aspects. CRC Press, Boca Raton, Fl.*

Rosenbeerg et al. 1994. Characterization of the Eosinophil Granule Proteins Recognized by the Activation–Specific EG2. J. of Leukocyte Biology. 56:502–506.*

Rosenberg et al. 1989. Human Eosinophil Cationic Protein. J. Exp. Med. 170:163–176.*

Tiffany et al. 1995. Hyperglycosylation eosinophil ibonucleases in a promyelocytic leukemia cell line and in differentiated peripheral blood progenitor cells. J. of leukocyte Bio. 58:49–53.*

Rosenberg et al. 1994. J. of Leukocyte Bio. 56:502–506.*

Reimert et al. J. of Immunological Methods. 138(2): 285–290.*

I. Olsson et al, *Blood*, vol. 67, No. 2, pp. 498–503 (Feb. 1986).

H. Rosenberg et al, *Journal of Leukocyte Biology*, vol. 56, pp. 502–506 (Oct. 1994).

* cited by examiner

DIAGNOSTIC METHOD FOR DETECTION OF MOLECULAR FORMS OF EOSINOPHILIC CATIONIC PROTEIN (ISO-ECPS)

TECHNICAL FIELD

The present invention concerns novel diagnostic methods involving determination of eosinophil cationic protein (ECP) and novel antibodies that can be employed in such methods.

TECHNICAL BACKGROUND

Eosinophil granule proteins have been suggested to mediate their cytotoxicity when in close contact with the target cells (Hamman et al., J. Immunol. 144 (1990) 3166–3173; Capron et al., Eosinophils in Asthma. London, New York, Tokyo: Acadmic Press (1989) 49–60; Robert et al., J. Allergy Clin. Immunol !1991) 1105–1115). ECP is a potent toxin for the larvae of Shistosoma Mansoni (McLaren et al., Parasitol. 88 (1984) 491–503) and a potent neurotoxin when injected into brains of guinea pigs or into the cerebrospinal fluid of rabbits (Fredens et al., J. Allergy Clin. Immunol. 70 (1982) 361–366). ECP is a membrane-active agent and may cause membrane damage. It induces ion flow through artificial bilayers by forming pores (Yong et al., Nature 321 (1985) 613–616).

Many investigators have shown (Olsson et al., Blood 44 (1974) 235–246; Olsson et al., Blood 67 (1986) 498–503; and Gleich et al., Pro. Natl. Acad. Sci. U.S.A. 83 (1986) 3146–3150) that purified ECP is separated on SDS-PAGE into different molecular weight forms (varying from 18 to 21 kDa). Peterson et al. (Eur. J. Haematol. 40 (1988) 415–423) showed that purified ECP from healthy donors was separated on SDS-PAGE into at least three molecular weight forms and their difference in charge and molecular weights were deduced to reflect different amounts of carbohydrates bound to the protein. Nothing is known about the biological activities of these various molecular forms of ECP (iso-ECPs).

It has long been known that eosinophilia is associated with a variety of inflammatory disorders including allergic disease. In such diseases eosinophils and their toxic products are seen in tissue specimens from inflammation foci, for instance asthma (Arm et al., Adv. Immunol. 51 (1992) 323–382). The cells and their granule products seem to be major causes of the tissue destruction, for instance shedding of epithelial cells in the airways (Filley et al., Lancet 3 (July, 1982) 11–16; Venge et al., Am. Rev. Resp. Dis. 138 (1988) 54–57; and Bousquet et al., N. Engl. J. Med 323 (1990) 1033–1039). The pathophysiological changes seen in the asthmatic lung leads to hyperactivity. Even a low grade inflammation seems to render the patients susceptible to a variety of challenges including allergen exposure (Bisgaard et al., J. Allergy Clin. Immunol. 85 (1990) 891–895) and exercise (Venge et al., J. Allergy Clin. Immunol. 88 (1991) 699–704). These conditions may be identified by the monitoring of activated eosinophils and their product ECP in various biological fluids.

Inflammatory conditions like acute asthma are treated by anti-inflammatory drugs (Sheffer, J. Allergy Clin. Immunol 88(Suppl) (1991) 425–534). The decline of inflammation, reflected by the level of ECP in blood samples, such as serum and plasma, may be of value in monitoring the effect of therapy.

ECP levels have been found elevated in other clinical conditions connected with activated eosinophils like atopic dermatitis (Kapp et al., J. Am. Acad. Dermatol. 24 (1991) 555–558), certain infections (Paganelli et al., J. Allergy Clin. Immunol. 88 (1991) 416–418), autoimmune conditions in the joints (Hällgren et al., Ann. Rheum. Dis. 43 (1984) 556–562), gut (Hällgren et al., Am. J. Med 86 (1989) 56–64) and in 30 parasitic disease (Venge et al., In. Eosinophil cationic proteins (ECP and EPX) in health and disease. Eds Yoshida et al., Immunobiology of the eosinophil. New York: Elsevier Biomedical (1983) 163–179).

THE DISCOVERY BEHIND THE INVENTION AND OBJECTIVES OF THE INVENTION

The invention is based on our discovery that isoforms of ECP (iso-ECPs) may create different biological effects, e.g. the cytotoxicity of ECP varies between isoforms. This has revealed to the inventors that improved human diagnostic methods are feasible by measuring iso-ECPs in biological fluids.

Consequently, the objectives of the invention are to provide novel and improved human diagnostic methods based on iso-ECP measurements, and reagents to be employed in these methods.

THE INVENTION

A. The Method Aspect

One aspect of the invention is a diagnostic method comprising the steps:
(a) measuring specifically the level of ECP in a sample derived from an individual to be diagnosed, and then
(b) comparing the ECP level found with a standard ECP level.

The characterizing feature of this aspect of the invention is that the level of at least one iso-ECP is selectively determined and compared with a reference level of the same iso-ECP. This aspect excludes the determination of the total amount (level) of all iso-ECPs.

The reference level may be the level found for apparently healthy individuals or a level obtained at an earlier occasion for the same individual. If the level found deviates from the normal level of healthy individuals, this is an indication that the individual suffers from some abnormal state, for instance states as described above (increased levels). In case the level differs from the level obtained at an earlier occasion for the same individual, the deviation indicates a change in state (recovery from or worsening of the abnormal state). In the latter case iso-ECP measurements will allow monitoring of medical treatment as discussed above. Decreased levels compared to the normal level may indicate overtreatment with ani-inflammatorials and/or eosinophil deficiency.

Preferred iso-ECPs to be measured are cytotoxic, such as the cytotoxic variant defined in the experimental section.

The expression "at least one iso-ECP is selectively determined" is meant to include also the sum of various isoforms of ECP, but not the total amount of ECP.

The measured level may be expressed as an absolute concentration (for instance $\mu g/L$ or nmol/L) or as a value relative some other sample constituents, for instance relative total amount of ECP, relative a certain iso-ECP combination or relative some other sample constituents.

The sample is derived from the human individual to be diagnosed and contains eosinophils and/or ECP. Due to the systemic presence of eosinophils, potential samples are broncho alveolar lavage fluid, blood (including serum and plasma samples), urine, cerebrospinal fluid, sputum, faeces, tear fluid and nasal fluid. Blood samples, for instance whole blood, serum and plasma samples, were at the priority date the preferred samples.

The measurement of iso-ECPs can in principle be performed by any method that is able to discriminate one or more iso-ECPs from other ECPs and to provide the sufficient sensitivity, precision and specificity etc. However as indicated in the experimental section, it is believed that immune assays are preferred.

An immune assay according to the invention means that the sample suspected of containing a deviating level of iso-ECPs is brought into contact with an anti-ECP antibody in an assay medium under conditions permitting formation of immune complexes incorporating ECPs and the anti-ECP antibody. Complexes containing the iso-ECPs to be determined is then determined by per se known methods to give a quantitative or qualitative measure of their level in the sample. In this type of assays the complex as such may be measured, or it may be measured by aid of a biospecific affinity reactant labelled with an analytically detectable substance (label), said reactant (and its label) being capable of becoming specifically incorporated into the complex. Suitable biospecific affinity reactants that can be labelled and employed are anti-ECP antibodies, with preference for those reacting specifically with one or more of the iso-ECPs to be measured, anti-antibodies directed against the constant regions of the anti-ECP antibody present in the complex formed, Proteins A and G etc. Examples of detectable substances (labels) that may be used are luminescers, chromophors, fluorophors, enzymes, enzyme substrates, cofactors, coenzymes, radioactive isotopes, particles (metallic or non-metallic), biotin (detected by its reaction with avidin/strepavidin) etc. Some labels change their signal when becoming incorporated into the immune complex while others do not. The former type of labels provides homogeneous immune assays in which there is no need to separate the label incorporated into the complex from the label not incorporated. The latter type of labels demands the separation to be carried out, for instance by insolubilizing the complex into which the label is incorporated (heterogeneous assays). In order to obtain an insolubilized complex that contains the label, precipitating agents, such as polyethylne glycol and insolubilized and insolubilizable biospecific affinity reactants binding to the complex may be used. This latter type of reagents must not insolubilize the labelled biospecific affinity reactant as such. The immune assays to be employed may also be of the competitive or non-competitive type. The latter type are often called sandwich assays because they utilises two antibodies that are able to bind simultaneous to the antigen (in our case ECP).

Known principles are applied to select the appropriate immune assay protocol, for instance homogeneous or heterogeneous variants, order and type of additions and incubation steps etc. The main point is that the amount of reactants added must be such that the amount of label incorporated into the complex or not incorporated into the complex will reflect the level of the iso-ECP(s) to be measured in the sample.

Normal assay conditions are aqueous media with or without water-miscible co-solvents, temperatures within 0–40° C. and pH-values within 4–10.

The term anti-ECP antibody (including an anti-iso-ECP antibody) means an antibody preparation reacting specifically with the intended iso-ECPs. An anti-ECP antibody to be used in the inventive diagnostic method has no substantial reaction with other components that may be present in the sample or assay medium. By the term "substantially no reaction" is meant that the antibody has no reactions destroying the intended purpose, in this case the result of the immune assay used.

Unless otherwise specified, the antibody concept above, in particular the anti-ECP/anti-iso-ECP antibody concept, also comprises antibody active fragments and derivatives, including Fab, $F(ab)_2$, Fv, single chain antibody etc, and any other biospecific affinity reactant binding specifically to ECP or selected iso-ECP(s).

In a preferred immune assay variant the anti-ECP antibody is specific only for the iso-ECPs to be measured, with further preference for monoclonal antibody preparations.

In case of using an anti-ECP antibody reacting with all iso-ECPs it is preferred to combine it in an sandwich assay with an anti-iso-ECP antibody that is specific for the iso-ECP(s) to be measured. In other case, the measurement of the relevant iso-ECP complexes has to be based on molecular iso-ECP differences that are retained in the complexes formed. Compare the assay variants presented in EP-A-535, 162 (Axis).

At the priority date the sandwich format with emphasis for the heterogeneous variants were preferred. Thus, the preferred assay variants makes use of two anti-ECP antibodies, at least one of them being able to discriminate between the iso-ECP(s) to be measured and other iso-ECPs. In the heterogeneous assay variants, one of the anti-ECP antibodies are or will, during assay, become bound to a solid phase (support) insoluble in the assay medium used.

The Inventive Anti-iso-ECP Antibody of The Invention

A second aspect of the invention is an anti-iso-ECP antibody binding specifically to an epitope that is unique for the native form of a cytotoxic isoform of ECP. Thus the inventive antibody in its binding to ECPs is able to discriminate at least one cytotoxic iso-ECP from other iso-ECPs and/or to at least partially inhibit the cytotoxic activity of the iso-ECP(s) to which the antibody binds. See the experimental section. At the priority date the preferred antibody preparation was specifically directed against an iso-ECP that is able to exert cytotoxicity against the erythroleukemic K562 cell line.

The inventive anti-iso-ECP antibody may be prepared by standard techniques well-known for other antibodies and comprises the same general types of antibody variants as described above. See also the experimental part.

EXPERIMENTAL PART 1

Isolation and Characterization of iso-ECPs and Monoclonal Antibodies

Methods
Isolation of Granules.

The granules were prepared from granulocytes of buffy coats obtained from healthy blood donors using a modification of the procedure described by Peterson et al (Eur. J. Haematol. 40 (1988) 415–423). The buffy coats, approximately 4 L, were mixed in measuring cylinders with an equal volume of 2% Dextran T-500 in NaCl/PBS (Phosphate Buffered Saline). The red blood cells were allowed to sediment for 1 h at room temperature before collection of the leukocyte rich plasma. The leukocytes were washed twice in PBS and once in 0.34 M sucrose by centrifugation at 400×g for 10 min. After the wash the leukocyte pellet was suspended in 5 volumes of 0.34 M sucrose. 300 mL of cell suspension mixed with an equal volume of 0.34 M sucrose were pressurized $N_2$ for 30 min at 750 psi with constant stirring in a nitrogen bomb (Parr Instrument Company, Moline, Ill., U.S.A.) at +4° C. (Klemper et al., J. Cell. Biol. 86 (1986) 21–28; and Borregard et al., J. Cell. Biol. 97 (1983) 52–61). The cavitate was then collected into an equal volume of 0.34 M sucrose, 0.34 M NaCl and centrifuged for 20 min at 450×g at +40° C. The supernatant was centrifuged for 20 min at 10,000×g at +4° C. to sediment the granules. After one cycle of freezing at 70° C. and thawing, the granule pellet was extracted with 5 volumes 50 mM acetic acid for 1 h at +4° C. An equal volume of 5 0.4 M sodium acetate, pH 4, was added and the extraction procedure was continued with magnetic stirring for 4 hrs at +4° C. The granule extract was then concentrated to approximately 5 mL using YM-3 filters (Amicon Corporation, Lexington, U.S.A.).

Chromatographic Procedures.

Gel filtration chromatography was performed on Sephadex® G-75 superfine column (Pharmacia Biotech AB, Uppsala, Sweden). The column was equilibrated with 0.2 M NaAc pH 4.5. The sample volume was approximately 5 mL and fractions of 3 mL were collected at a flow rate of 7 mL/h. Protein was determined by its absorption at 280 nm.

Ion exchange chromatography was performed using the FPLC and a strong cationic exchanger Mono-S prepacked column (Pharmacia Biotech AB). The column was equilibrated with 50 mM MES (2-[N-morpholinol] ethane sulphonic acid) betain 2% 0.1 M LiCl, pH 6.0 (starting buffer). The sample (2 mL of pool 8 (see FIG. 1)) in starting buffer was loaded and eluted using a linear gradient from 0.1 M to 1.0 M LiCl, pH 6.0.

Periodate Treatment.

Pool 8 of the ECP preparations after gel chromatography on Sephadex® G-75 (see FIG. 1) was incubated with sodium metaperiodate in 0.1 M sodium acetate buffer pH 4.5 (Peterson et al., Eur. J. Haematol. 40 (1988) 415–423; and Stewart et 30 al., Proc. Natl. Acad. Sci. U.S. A. 74 (1977) 4200–4204) at a molar ratio 1:1600 for 17 hrs at +4° C.

Protein Determinations and Concentrating Protein Solutions.

Proteins in the chromatograms were measured by their absorbance at 280 nm. Specific proteins were measured with a radioimmunoassay (see below). Ultrafiltration of pooled fractions was performed on an YM-2 filter (Amicon Corporation, Lexington, U.S.A). Buffer exchange was performed by using PD-10 columns (Pharmacia Biotech AB). Protein pools were stored in 0.2 M sodium acetate, pH 5.5, −70° C.

Electrophoretic Procedures.

Discontinuous sodium dodecyl sulphate polyacryl amide gel electrophoresis (SDS-PAGE) was performed by using the PhastSystem (Pharmacia Biotech AB), PhastGel Gradient 10–15%. Molecular weight markers were phosphorylase b (94 kDa), albumin (67 kDa), ovalbumin (43 kDa), trypsin inhibitor (20 kDa) and lactalbumin (14,4 kDa). After electrophoresis, the gels were stained with Coomassie Brilliant Blue R-250 by using the PhastSystem.

Immunoblotting of granule proteins was performed by using the PhastTransferSemi-dry Electrophoretic Transfer System (Pharmacia Biotech AB). After SDS-PAGE, proteins were electrophoretically transferred to nitro-cellulose paper for 30 min at 20 V and 25 mA. The transfer buffer was 25 mM Tris, 0.192 M glycine, 20% methanol. Transferred proteins were incubated with mouse antibodies to purified granule proteins diluted 1:2,000 and immune complexes were then identified by alkaline phosphatase conjugated antibodies to mouse IgG (Sigma Immunochemicals, CO, U.S.A.) and stained by 25 mg (α-naphthyl phosphate. 25 mg o-dianisidine, tetrazotized (Sigma) diluted in 50 mL 0.06 M borate buffer pH 9.7.

Antibodies against ECP and EPO.

Monoclonal antibodies (mAb) against ECP and EPO were produced using the hybridoma technique. Briefly, Balb/c mice were immunized with 50 μg of purified antigen in adjuvants followed by boosters of 25 μg of antigen during 3 consecutive days. After fusion of spleen cells with Sp2/0 myeloma cells, the supernatants were screened for antibodies against ECP and EPO, respectively, by analysis in ELISA. Monoclonal antibodies against ECP were further characterized by BIAcore® (Pharmacia Biosensor, Uppsala, Sweden) for their epitope specificity. Four clones of various epitope specificity on ECP (cl 611, 612, 614 and 652) and one reactive against EPO were selected for expansion and purification. All antibodies were of the IgG1 subtype.

Radioimzmunoassay (RIA) of ECP.

ECP concentrations in the individual column fractions were determined by the use of Pharmacia ECP RIA (Pharmacia Diagnostics, Uppsala, Sweden).

Cytotoxicity and Inhibition of Toxicity Assays.

FMCA Procedure. A modification of the fluorometric microculture cytotoxic assay (FMCA) described by Larson et al., (Int. J. Cancer 50 (1992) 177–185) were used. The erythroleukemic K562 cell line was cultured in RPMI 1640 supplemented with 10% heat inactivated fetal calf serum (FCS), penicillin 5,000 U/mL and streptomycin 5,000 g/mL. By the day of assay the cells were washed three times in RPMI 1640 supplemented with penicillin 5,000 U/mL and streptomycin 5,000 g/mL and without FCS. K562 cells, 20,000 cells/well, were seeded into wells of V-shaped 96-well microtiter plates (Nunc, Roskilde, Denmark) in triplicates, and 10 μl ECP in 0.2 M Na-acetate buffer pH 5.5 at a final concentration of 20 μg/ml/well was added. As controls served wells with cells and buffer. The culture plates were then incubated at 37° C. in humidified atmosphere containing 95% air and 5% $CO_2$ for 72 hrs, followed by centrifugation (200×g, 7 min). After medium removal and one wash with PBS 200 μl/well, 100 μl/well of PBS containing FDA (10 μg/ml; fluorescein diacetate (Sigma, St Louis, Mo., U.S.A.)) was added. Subsequently the plates were incubated for 1 hr at 37° C. before reading fluorescence at 485 nm (Fluorescan 2, Labsystems Oy, Helsinki, Finland). The fluorometer was blanked against wells containing PBS including FDA dye but without cells. The fluorescence data was transferred to custom-made software for automated data calculation using Microsoft Excel and MacIntosh SE/30 personal computer. The results obtained by the indicator FDA are presented as survival index (SI) defined as fluorescence in test wells in per cent of control wells. Individual column fractions were tested for toxicity to K562 cells.

DiSC Procedure. In parallel a short-term dye-exclusion test, Differential Staining and Cytotoxicity (DISC) assay (Weisenthal et al., Cancer Res. 43 (1983) 749–757; and Nygren et al., Leukemia 11 (1992) 1121–1128) was performed. Immediately after fluorescence measurement, selected wells were exposed to a mixture of Fast green (1%, Sigma), Nigrosin (0.5%, Sigma), and 25,000 formaldehyde-fixed chicken erythrocytes/well for 10 min at room temperature. The cellular content of the wells was subsequently cytocentrifuged onto slides and counterstained with May-Grunewald-Giemsa stain. Cell survival was evaluated by light microscopy. Viable cells stain normal Giemsa morphology, whereas dead cells and chicken erythrocytes stain greenish-black. Tumor cell survival using this modified DiSC procedure (Nygren et al., Leukemia 11 (1992) 1121–1128) was calculated by expressing the survival index (SI) as the ratio of viable K562 cells to fixed chicken erythrocytes in experimental wells as a percentage of the ratio obtained in control wells.

Inhibition K562 cells were prepared, see above, 180 µl/well. Antibodies against ECP, 10 µl, were added at a final concentration of 100 µg/ml/well and ECP 10 µl were added at a final concentration of 20 µg/ml/well were added.

Statistics.

For the statistical evaluation of differences between the groups, the Mann-Whitney U-test and Wilcxon's test for paired samples were used. Calculations were made on a personal computer with use of the statistical package, Statistica/W(StatSoft, Tulsa, Okla., U.S.A.).

Results
Molecular Properties and Cytotoxic Activity of Pools from Gel Chromatography on Sephadex® G-75

Supernatants from extracted granules from healthy blood donors were subjected to gel filtration on a Sephadex® G-75 column (FIG. 1) and eluted with 0.2 M NaAc, pH 4.5. ECP in the fractions was measured by means of a specific RIA (Peterson C. G. B. et al., Clin. Exp. Allergy 21 (1991) 561–566). Fractions were pooled as indicated and ECP in pools 7 and 8 were concentrated by ultrafiltration. The insert in FIG. 1, shows a SDS-PAGE of proteins in pool 7 and pool 8. In pool 7 two bands at approximate molecular weights of 21 and 24 kDA were seen. After reduction the two bands had molecular weights around 20 and 22 kDa. In pool 8 one major band was found at 22 kDa after reduction two bands of molecular weights of 18 and 15 kDa were found. All bands, before reduction, were identified as ECP by means of Western Immunoblots using various monoclonal antibodies against ECP.

In FIG. 2, the cytotoxic activity of pool 7 (n=10) and pool 8 (n=12) after gel filtration is shown. The cytotoxic activity of ECP was significantly higher in pool 8 (p<0.01) with only a minor activity in pool 7.

Molecular properties and cytotoxic activity of pools from FPLC chromatography on a Mono-S column.

The protein in pool 8 (Mw 20 kDa) from the gel filtration above was separated on a Mono-S column (FIG. 3). Fractions were pooled as indicated and concentrated, and the amount of ECP in each pool was measured as indicated in the figure. Three major ECP-containing pools were obtained, pools V, VI and VII. SDS-PAGE of the proteins in these pools showed without reduction a double-band in pool V with Mws of 20 and 22 kDa, respectively. In pool VI a single, but very broad band of Mw of 19–21 kDa was seen. Pool VII contained one single band at a Mw of 20 kDa. After reduction a similar pattern was obtained, but with a slight shift (1–2 kDa) of all bands to lower Mws and in addition a low Mw protein of about 15 kDa (FIG. 4). The identification of the proteins in these three pools before reduction (FIG. 5a) as ECP was established by means of Western Immunoblots and is shown in FIG. 5b. The results with mAb614 against ECP are shown and identical results were obtained with mAb611 and mAb612 (not shown). Thus, all of the above-presented bands were identified as ECP. In addition a high Mw protein, about 30 kDa, was also identified (FIG. 5b), which was not visible on protein staining of the gel. With the mAb652 only the bands at Mws in the range of 19–22 kDa were identified (FIG. 5c).

The cytotoxic activity of the pools V, VI and VII from five different Mono-S preparations is shown in FIG. 6. Cytotoxic toxicity against K652 was predominantly found in pool V with only one of the preparations of the other pools having cytotoxic activity.

Antibody Inhibition of the Cytotoxic Activity.

The inhibition of the cytotoxic activity of pool 8 after gel filtration on Sephadex® G-75 by various antibodies is shown in FIG. 7. The polyclonal rabbit ECP-antibody, but not the EPOant-ibody, neutralized the toxic activity by about 98%. When the inhibitory effect of mAb611, mAb612, mAb614 and mAb652 against ECP was tested, mAb 652 caused a 90–98% inhibition, whereas the other monoclonal antibodies were without effect. Also the commercially available monoclonal antibodies against ECP, i.e. EG1 and EG2, were unable to inhibit the cytotoxic activity of ECP. In one experiment the cytotoxic activity of pool V from FPLC chromatography on Mono-S, was also neutralized by mAb652 but not by the other mAbs (not shown).

Protein Deglycosylation.

The cytotoxic ECP (pool 8) from the gel filtration was incubated with sodium periodate at a molar ratio of 1:1600 before separation on a Mono-S column (FIG. 8a). Fractions were pooled as indicated and concentrated and the amounts of ECP in each pool were measured as indicated in FIG. 8a. The charge of the three major ECP-containing peaks changed into more basic molecules after periodate oxidation. SDS-PAGE of the proteins (FIG. 8b), however, showed virtually unaltered olecular sizes.

Preparation of ECP from One Single Iindividual.

ECP was also prepared from one single individual with hypereosinophilia. Also in this single individual we found a certain degree of molecular heterogeneity, but no cytotoxic activity of ECP purified on Mono-S. The SDS-PAGE of the Mono-S pools eluting at the same ionic strength as above revealed bands of ECP at 20 kDa, but no 22 kDa protein band (FIG. 9).

Treatment with Protease Inhibitor.

Since the heterogeneity with respect to size might be due to protease degradation during purification of ECP, purification in all steps was performed in the presence of the protease inhibitor phenylmethylsulfonyl fluoride (PMSF) at a concentration of 100 µg/ml. This procedure did not change the molecular heterogeneity of ECP nor did it affect the cytotoxic activity of ECP.

Discussion

The data presented has shown the existence of several molecular variants (isoforms) of the eosinophil cationic protein (ECP) with differences in biological activity. Our data also suggest that the molecular heterogeneity is partly dependent on differences in glycosylation, but that the molecular variant with cytotoxic activity has a unique structure not shared by the other variants. Furthermore it has been possible to produce monoclonal antibodies specifically neutralizing the cytotoxic activity of this variant.

Purification of ECP included two steps, gel filtration and cation exchange chromatography on Mono-S. On gel filtration ECP eluted in an irregular peak, which already at this step suggested a heterogeneity. After this crude separation it became obvious that the cytotoxic activity was associated with lower molecular weight species of ECP. We focused therefore in this study on the definition of the cytotoxic molecules in this lower molecular weight region. Upon further purification on Mono-S, we found basically three peaks containing ECP, which on SDS-PAGE showed a consistent pattern. Thus, the most basic ECP variant came out on SDS-PAGE as a single band with an approximate molecular weight of 20 kDa, whereas the least basic consistently came out as a distinct double band with molecular weights of approximately 22 and 20 kDa, respectively. The molecular species of ECP in between always came out as a broad band in the same molecular weight region. Reduction showed the appearance of a 15 kDa-band in peaks V and VI, whereas deglycosylation with periodate oxidation did not change the appearance on the gels significantly. The charge of all variants, however, changed after periodate oxidation into more basic molecules. These results indicate that the heterogeneity of ECP from these three Mono-S peaks cannot be explained by major differences in glycosylation and that there exist -S—S-bridges in the molecule that may determine the tertiary structure. All monoclonal antibodies against ECP showed on immunoblot that the different bands before reduction shared epitopes, which confirm that they were all ECP molecules. The monoclonal antibodies, mAb 611, 612 and 614, but not 652, however, also identified one band, barely visible after protein staining at a molecular weight of approximately 30 kDa, in particular preparations of peaks VI and VII, i.e. the peaks containing the two most basic and non-cytotoxic variants of ECP. Our data indicate that the cytotoxic variant of ECP has some unique molecular properties, which determine its cytotoxic activity. If both molecular species found in this cytotoxic preparation are necessary for the cytotoxic activity is not known at present, but the fact that the absence of the high molecular weight band in a preparation from one patient with eosinophilia also made this ECP preparation non-cytotoxic suggests that this 22 kDa species is a necessary part.

In this study we have shown consistently the presence of 5–6 variants of ECP, and the questions we asked were whether these variants were a consequence of the purification procedure or whether they were genetically determined. The former cause is very unlikely, since the heterogeneity was not different from preparations of ECP in the presence of protease inhibitors. Also the variants are very consistently found in most preparations. The latter question, however, is a distinct possibility, which can not be ruled out. Thus, our starting material for the preparation of ECP was always pools of normal leukocytes. These pools were in general obtained from about 100 randomly selected blood donors each of which may have their distinct variant of ECP. This was at least true for one of the patients from which eosinophils were obtained, since the heterogeneity of ECP obtained from this patient was considerably less. Another possibility is of course that these variants partly represent posttranslational changes of the molecule due to differences in their extent of glycosylation and that these changes are the consequences of non-genetically determined factors.

The finding that mAb652, which uniquely neutralized the cytotoxic activity of ECP, identified epitopes in all ECP-species irrespective of their cytotoxic activity, indicates that the cytotoxic epitope is present in all ECP variants. The cytotoxic site in ECP may therefore be related to some unique structural property of the molecule. It is, however, intriguing that mAb652 did not identify the 30 kDa band, which was barely seen in the preparations of the cytotoxic ECP. Based on our results we propose that the cytotoxic capacity of ECP is related to the 22 kDa variant found in peak V after separation on Mono-S. This molecule has a certain degree of glycosylation and an internal S—S bridge. The molecule may also contain a labile proteolytic site, since part of ECP is reduced to a 15 and 7 kDa band. This 15 kDa chain might through dimerization form the 30 kDa protein revealed on immunoblot. This 30 kDa protein does not react with mAb652, but with the other monoclonals, and may therefore have lost the cytotoxic site of ECP, which accordingly is related to the 7 kDa chain. On top of these molecular variants, many other variants are formed due to the differences in degree of glycosylation. It is also deduced from our results that more than one gene product of ECP may exist.

In earlier studies we showed that two other monoclonal antibodies, EG1 and EG2, bound to ECP in non-activated and activated eosinophils, respectively. These differences were shown to be related to the capacity of the antibodies to recognize ECP at different degrees of glycosylation, since EG2 on immunoblot only detected low-molecular weight and deglycosylated ECP. Our present results, however, show that none of these monoclonals are able to neutralize the cytotoxic activity of ECP, which means that the cytotoxic site is distinct from the proposed matrix-binding site of ECP and that he cytotoxicity is not simply related to the deglycosylated ECP molecule.

EXPERIMENTAL PART II

ISO-ECP Assays on Clinical Material

Test Kits

Assays were performed on various clinical materials with sandwich ECP assays in which the ECP antigen is complexed between a solid phase anti-ECP antibody and a labelled anti-ECP antibody. A comparison was made between the established method Pharmacia CAP System ECP FEIA (Pharmacia Diagnostics, Uppsala, Sweden) and the same kit but with the solid phase bound antibody and the labeled antibody being replaced with mab614 and mab652, respectively.

Results

See legends to the figures.

LEGENDS TO THE FIGS

FIGS. 1–9 corresponds to experimental part I and FIGS. 10–13 correspond to experimental part II.

FIG. 1

Gel filtration chromatography on Sephadex® G-75 of granule extracts obtained from healthy blood donors. Radio-immunoassay of ECP is included in the chromatogram. Protein in the peaks was pooled as indicated at the bottom of the chromatogram. The insert shows the SDS-PAGE pattern of the pools 7 and 8 (reduced and unreduced) from the chromatogram. R =molecular weight markers were phosphorylase b (94 kDa), albumin (67 kDa), ovalbumin (43 kDa), carbonic anhydrase (30 kDa), trypsin inhibitor (20.1 kDa) and α-lactalbumin (14.4 kDa). Samples were stained with Coomassie Brilliant Blue R-250.

FIG. 2.

The cytotoxic activity in pools 7 and 8 after Sephadex® G-75 gel filtration. Cells from the cell line K562 were seeded into the wells of 96-well microtiter plates, 20,000/well. ECP from different preparations was used at a final concentration of 20 μg/mL/well followed by incubation and measurement of fluorescence by means of the FMCA procedure as described under Materials and Methods. For calculation of Survival Index (SI) and P values, see Methods above.

FIG. 3.

Ion-exchange chromatography on a Mono-S column of pool 8 from gel filtration on Sephadex® G-75. The sample (2 mL of pool 8) was loaded in starting buffer and eluted as indicated in Materials and Methods. Fractions were pooled as indicated at the bottom of the chromatogram (1–7). Bars indicate the amount of ECP in the pools as determined by means of RIA.

FIG. 4.

Reduction of proteins from pools V, VII and VII in FIG. 3 (Mono-S column). Mw markers are found in lane R. + indicates reduced proteins and − indicates unreduced proteins.

FIGS. 5a–c.

The pools V, VI and VII in FIG. 3 (Mono-S column) were identified on (a) SDS-PAGE and (b, c) by means of immunoblot. (a) Mw markers in lane R. Lanes V, VI and VII (unreduced) correspond to purified ECP from respective pool according to FIG. 3. (b) Proteins identified by mAb 614. (c) Proteins identified by mAb 652. Unreduced samples were run on SDS-PAGE followed by transfer to nitrocellulose paper.

FIG. 6.

Comparison of the cytotoxic effect to K562 cells of ECP after chromatography on Mono-S (pools V, VI and VII, five individual preparations). Results are expressed as survival index (%) using the FMCA procedure.

FIG. 7.

Antibody inhibition of the cytotoxic activity. The dots indicate the means of three duplicate measurements. The bars are the median values of the three duplicates.

FIGS. 8a–b a. Chromatogram for separation of pool 8 (as defined in FIG. 1) on a Mono-S column, before and after periodate oxidation of the proteins. Unbroken lines indicates the chromatography of periodate treated material and the dotted line the chromatography of the untreated material. The bars indicate the concentration of ECP as measured by RIA after periodate treatment. The broken line indicates the LiCl gradient.

b. SDS-PAGE of proteins from the chromatogram in FIG. 8a before and after periodate oxidation. Mw markers are indicated in lane R and lanes V, VI and VII correspond to purified ECP from the respective pools as shown in FIG. 8a. +=material treated with periodate, and −=untreated material.

FIG. 9.

SDS-PAGE of ECP purified by chromatography on a Mono-S column from one individual with hypereosinophilia. Mw markers are found in lane R and the samples for lanes V, VI and VII correspond to pools V, VI, VII of normal eosinophils as shown in FIG. 3.

FIGS. 10 and 11.

These show the serum levels of ECP, as measured by the established method and as measured with the inventive method for the detection of iso-ECP.

r=referrence group, 99 healthy non-allergic subjects.

aa=acute asthma, some treated and some untreated, n=17.

ka=cat allregic children after three years of hyposensitization, n=24.

e=European study on asthma and allergy, mixture between treated and untreated patients, n=42.

sj=Patients with Sjögren's syndrome, mostly untreated, n=9.

bl=a mixed group of patients referred to hospital for complaints of allergy and asthma, n=22.

i=a group of patients with acute viral and bacterial infections, n=113.

p=allergic patients before and during a pollen season, n=57.

g=patients with chronic asthma, untreated, n=15.

FIG. 13 shows the serum levels of ECP in healthy references.

Figure 1A:
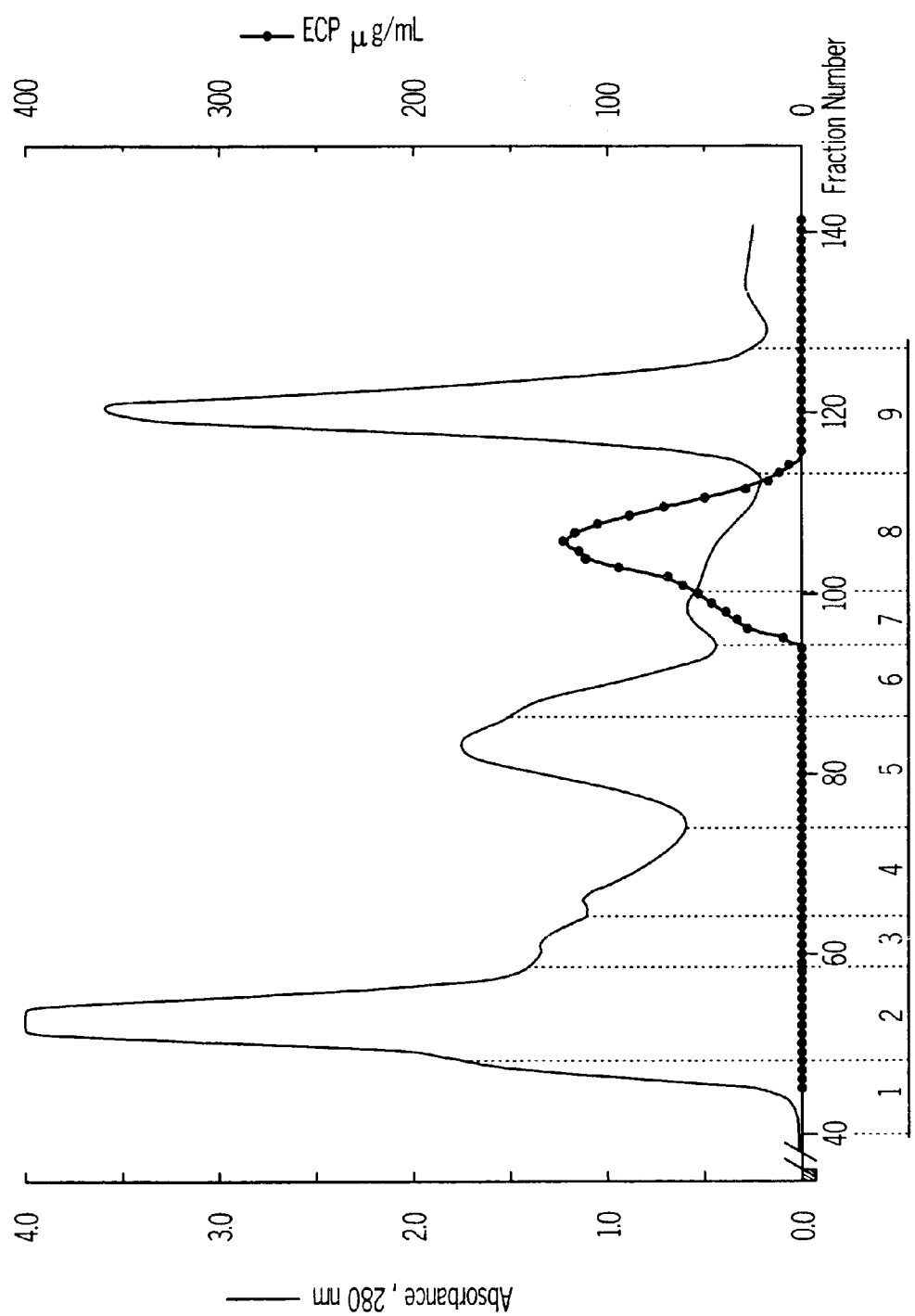
Figure 1B:
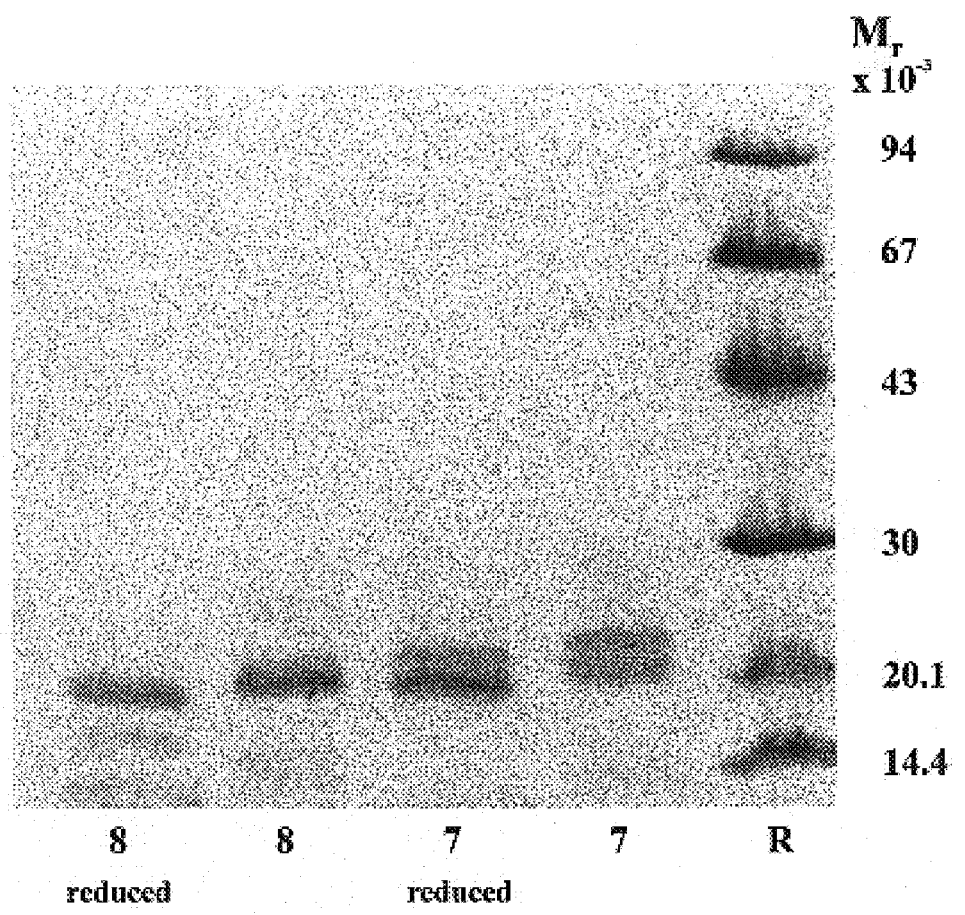
Figure 2:
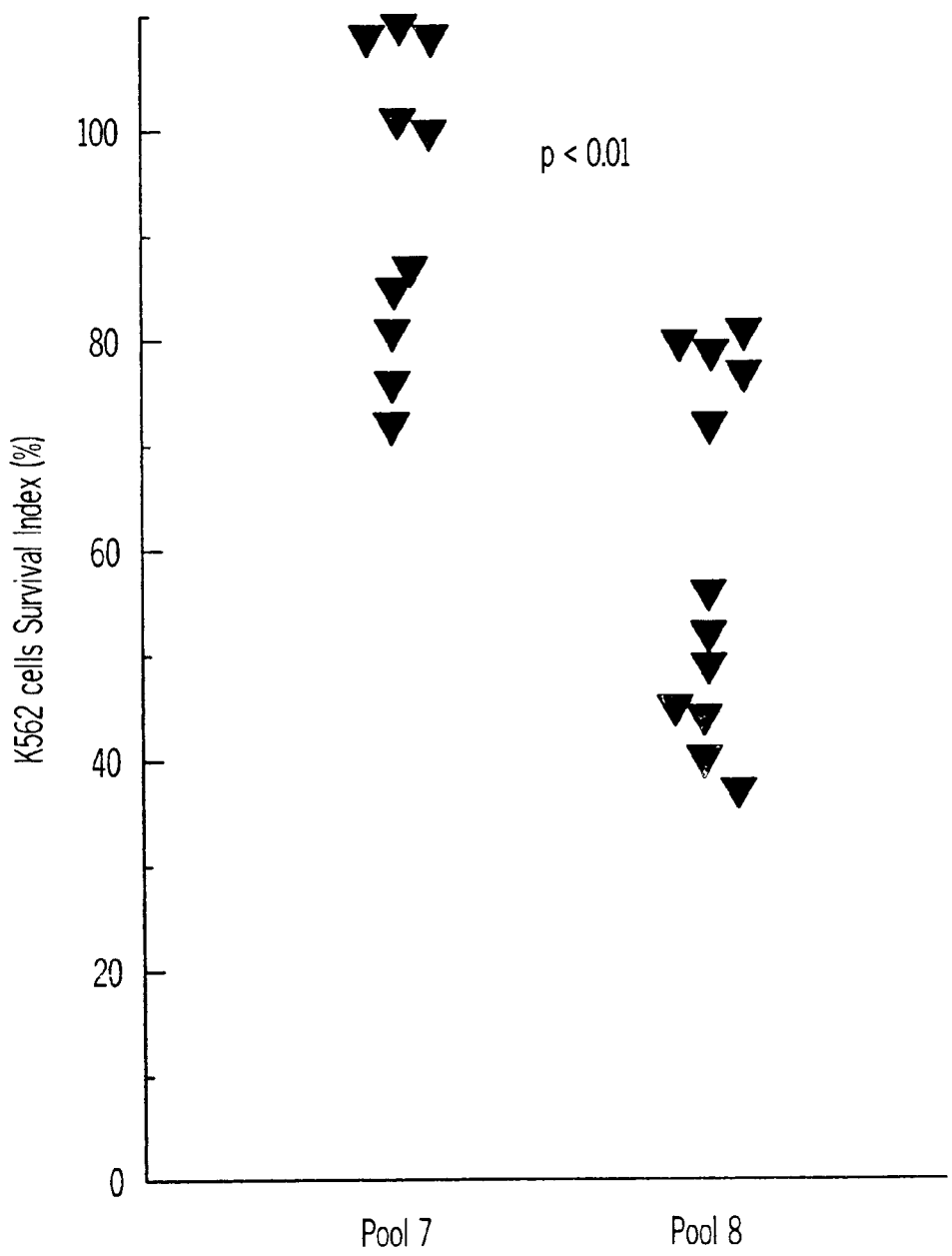
Figure 3:
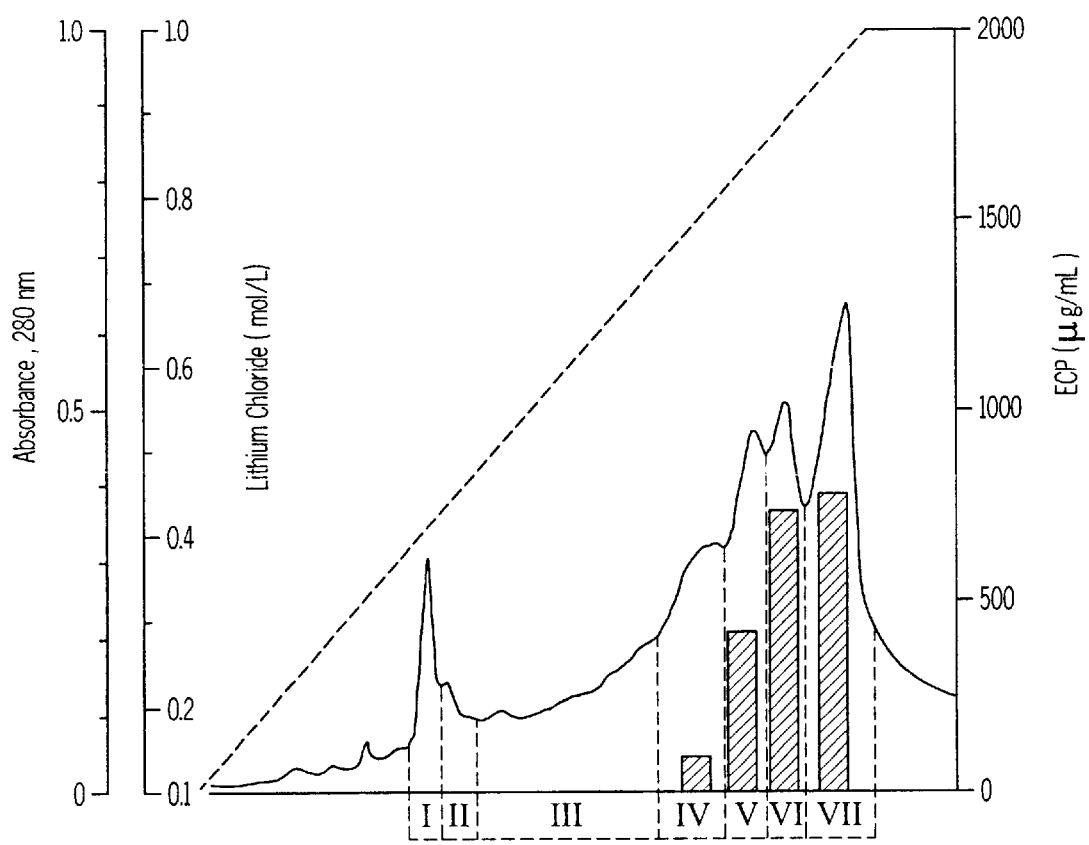
Figure 4:
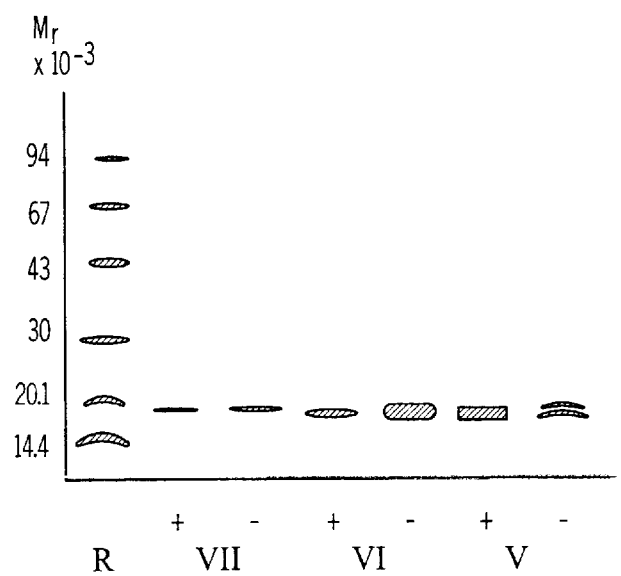
Figure 5:
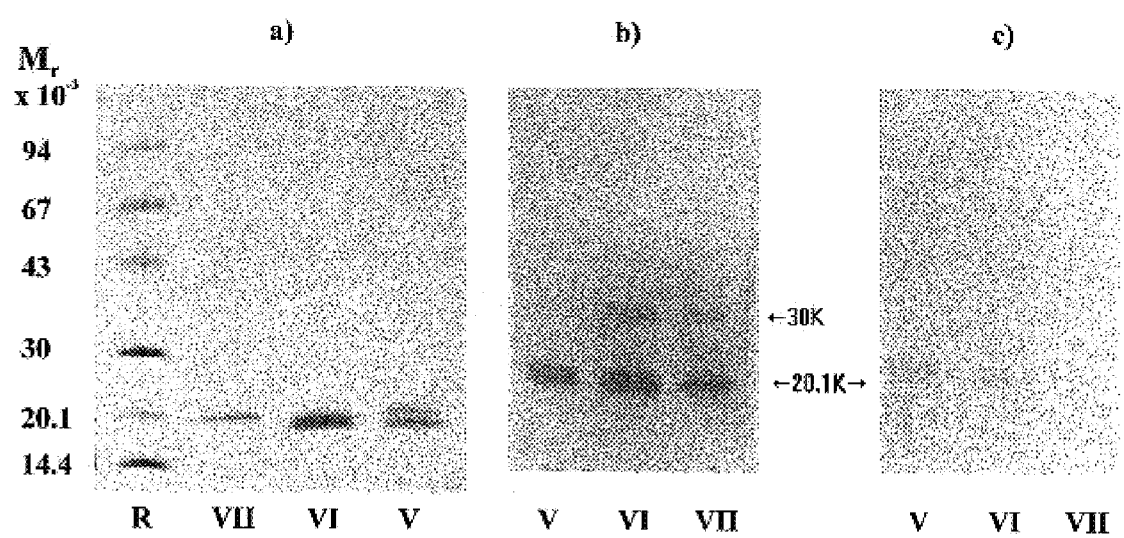
Figure 6:
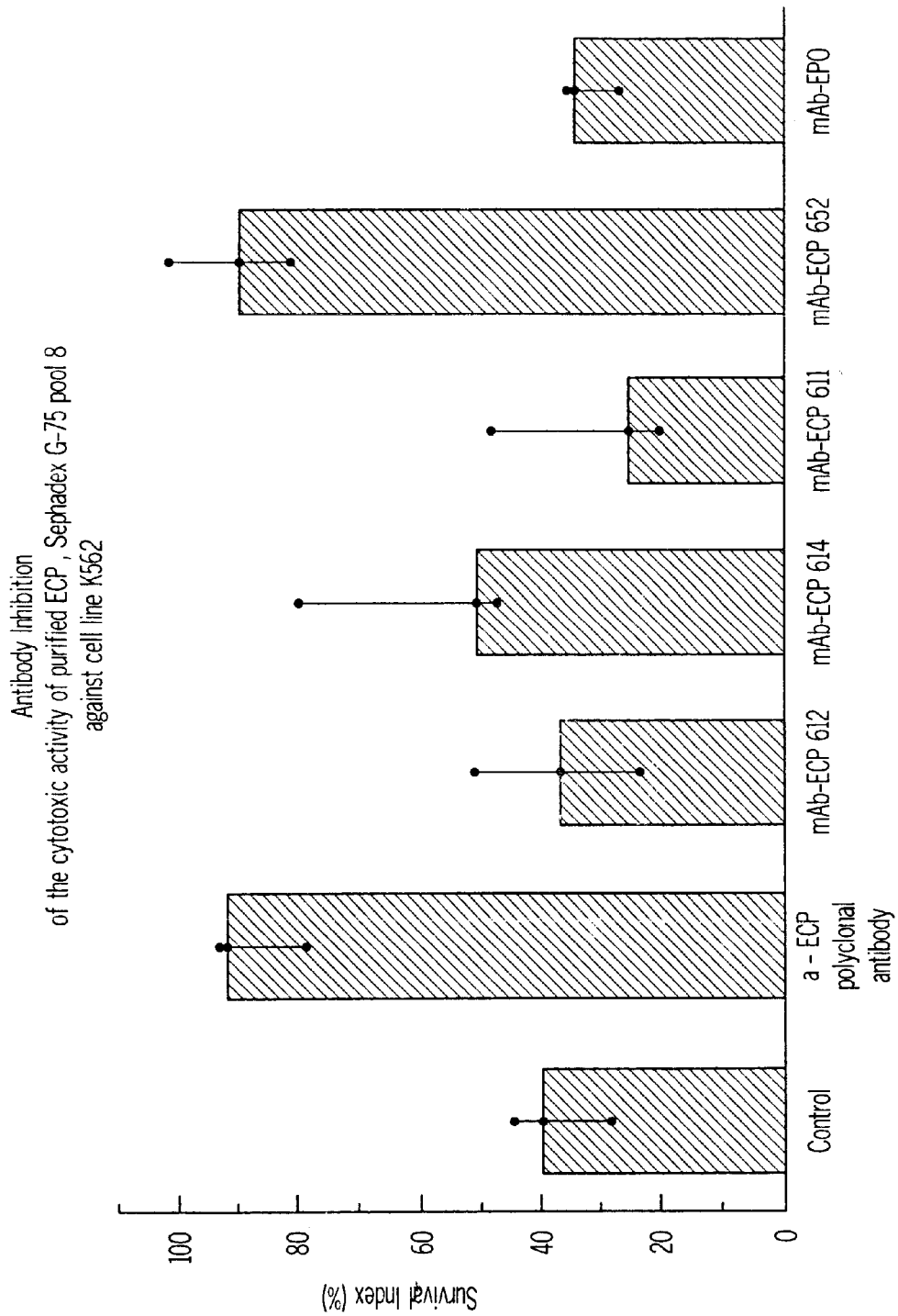
Figure 7A:
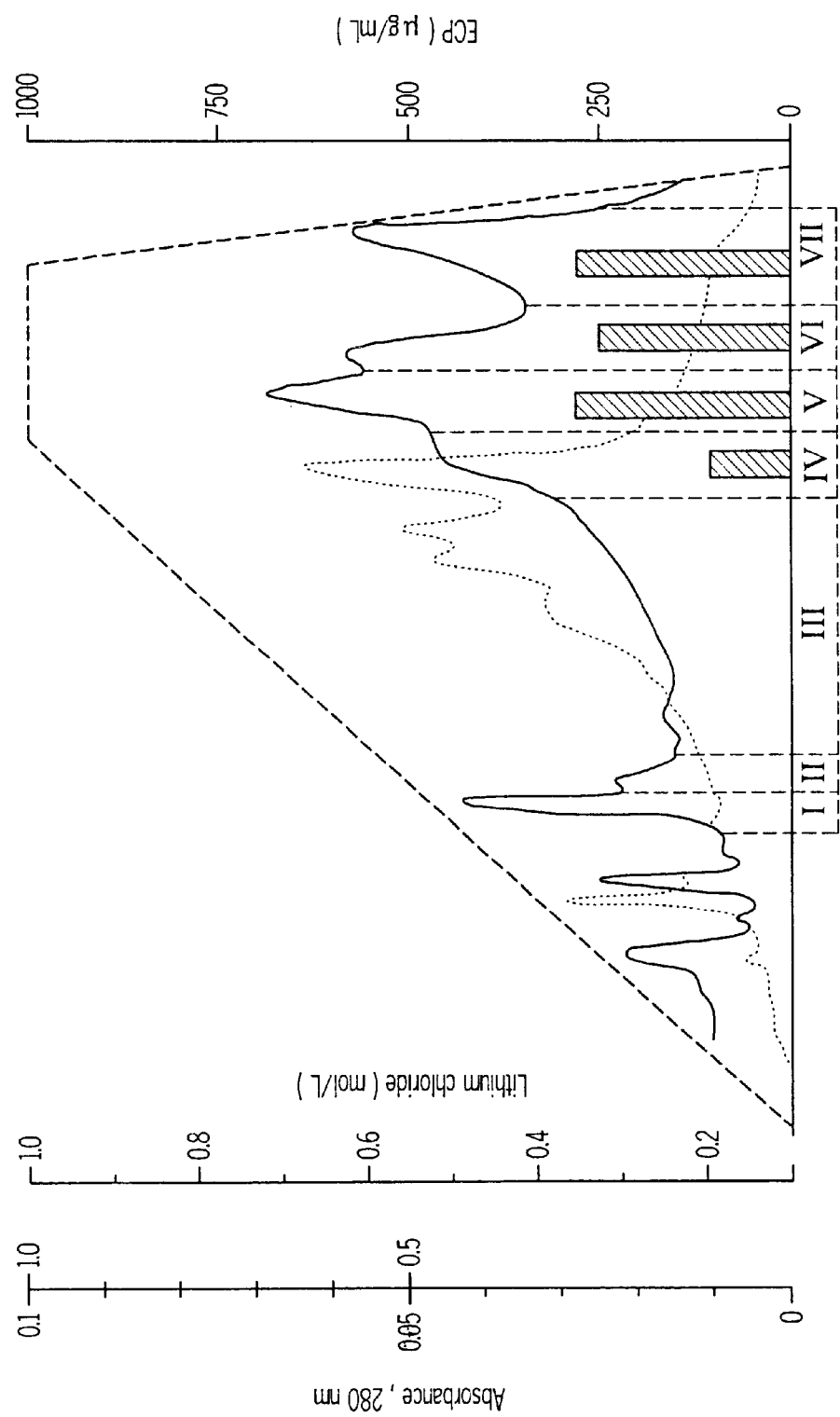
Figure 7B:
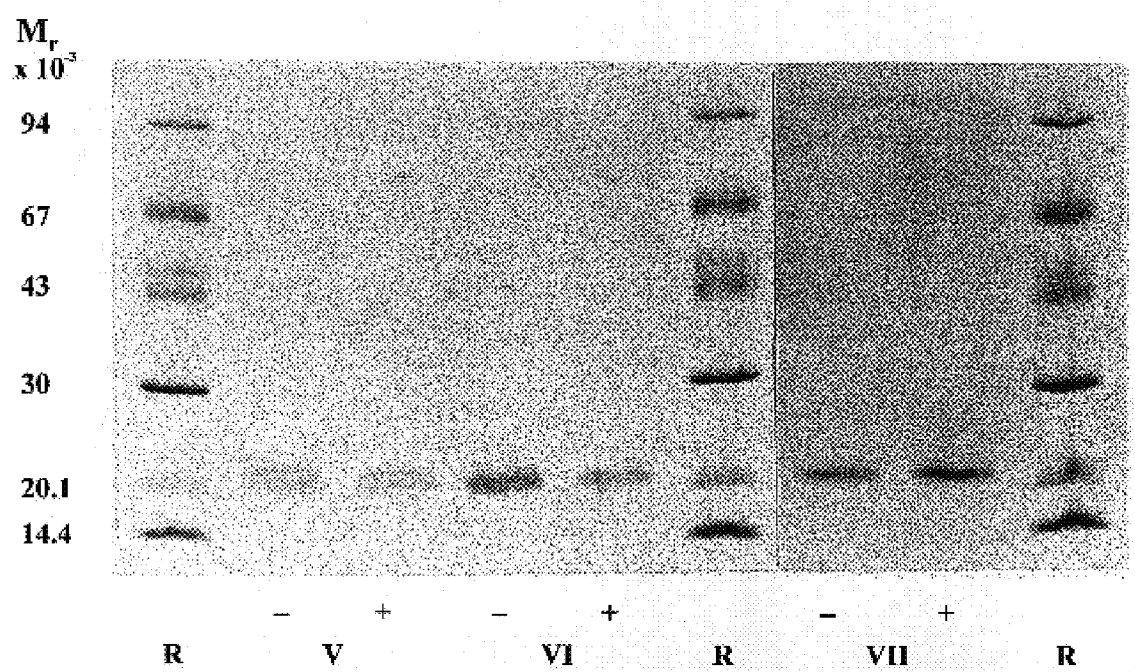
Figure 8:
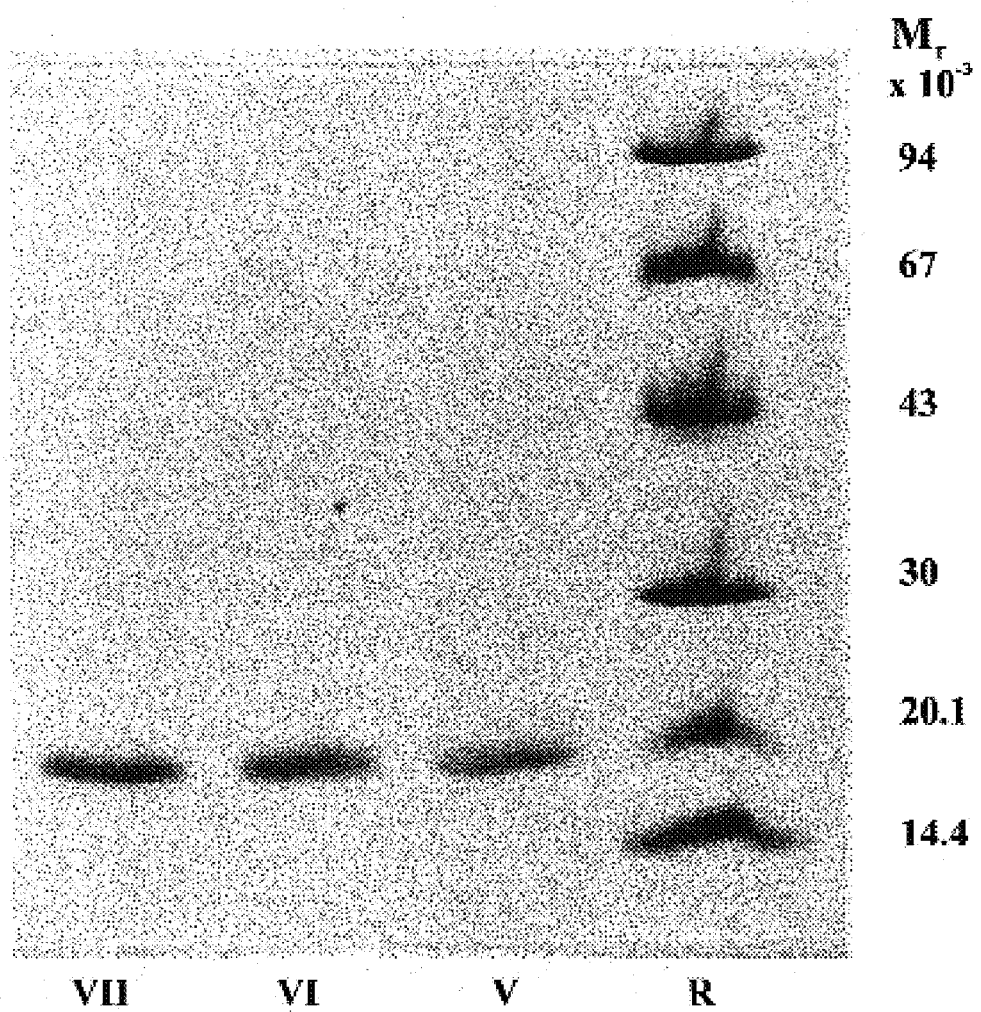
Figure 9:
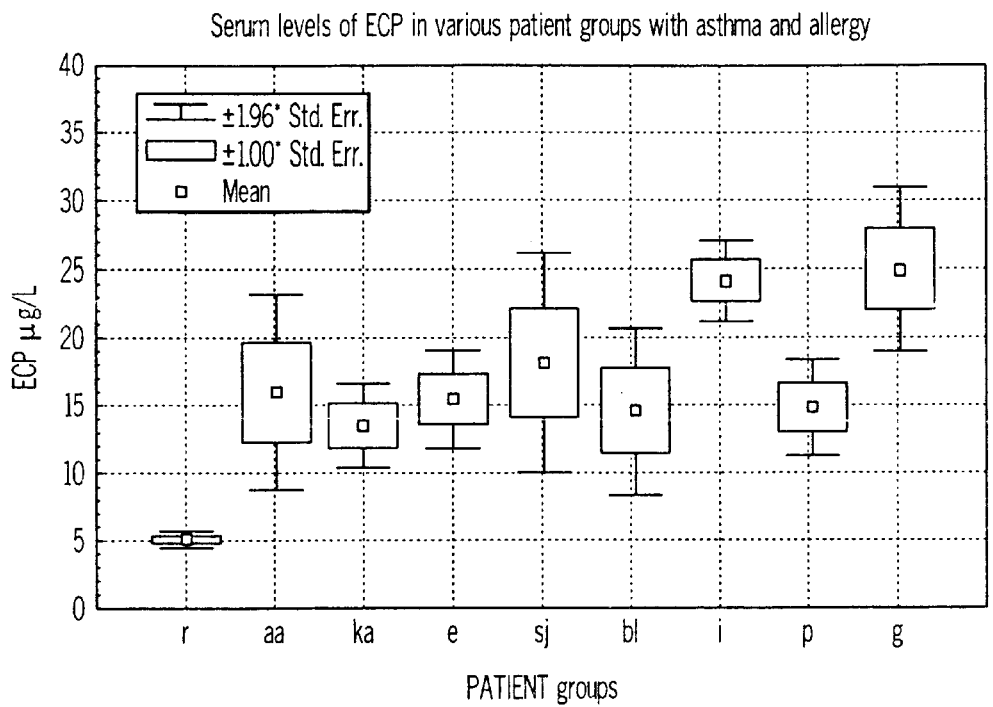
Figure 10:
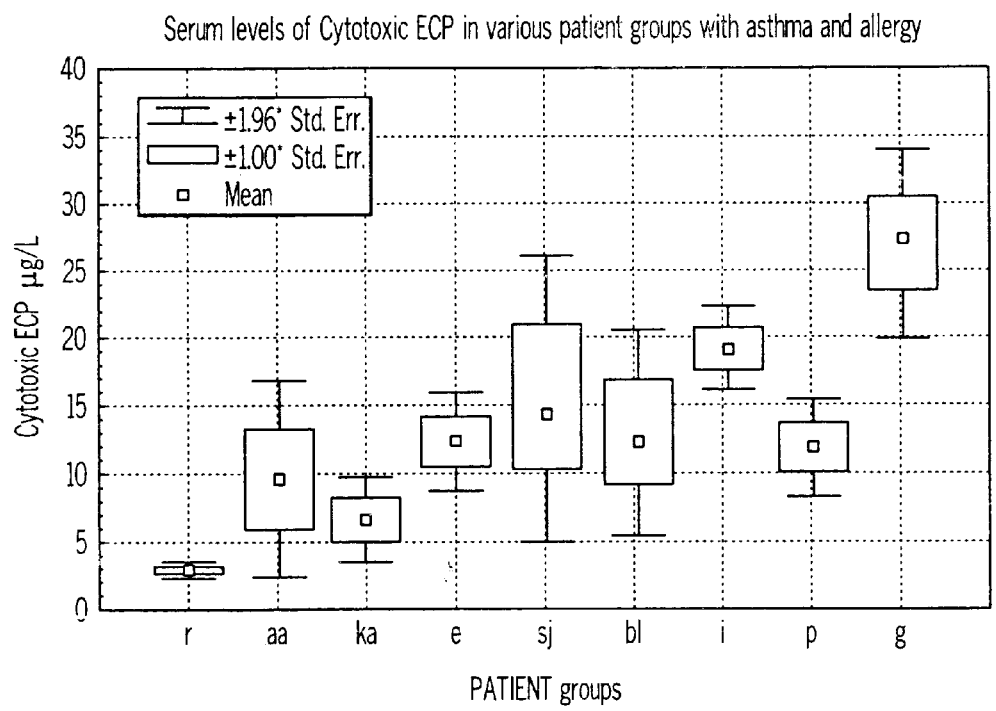
Figure 11:
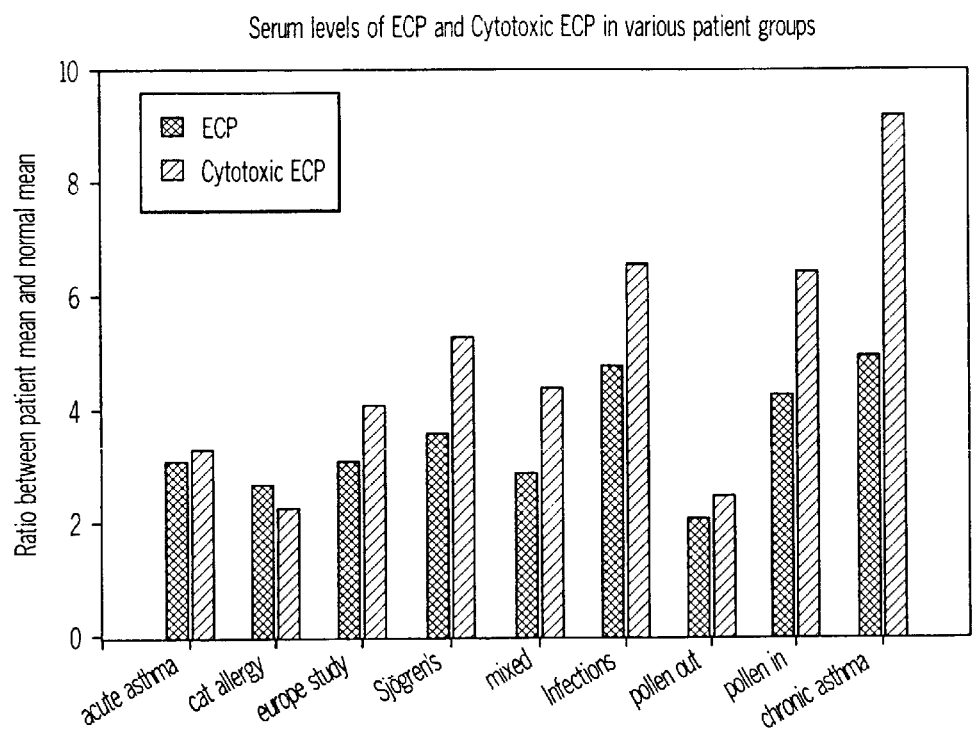
Figure 12:
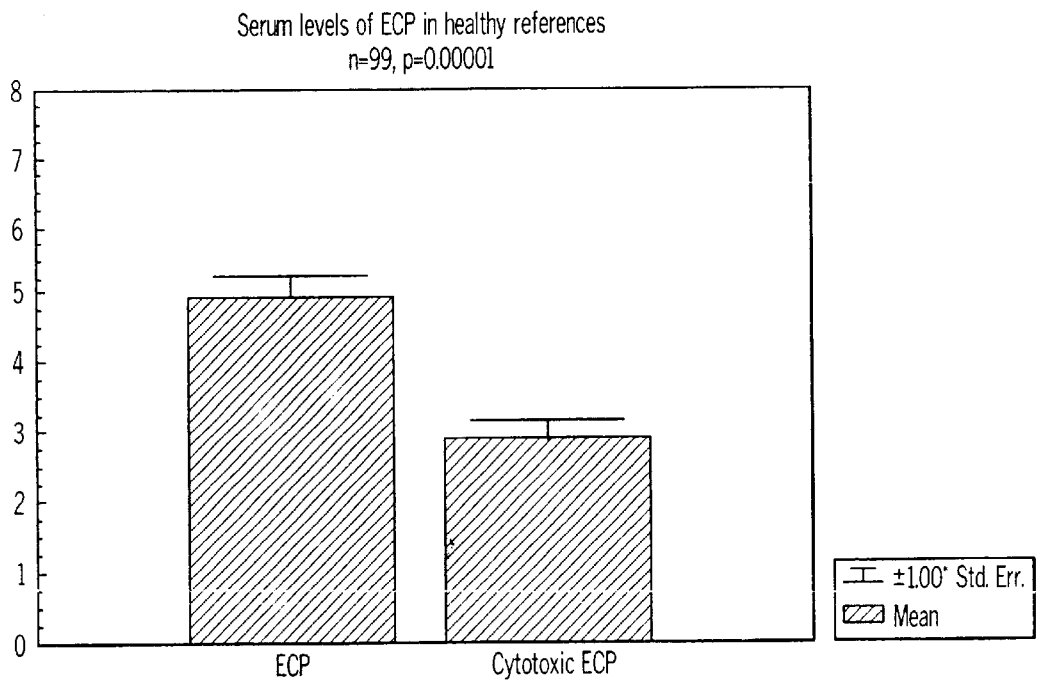
FIG. 12 shows the ratios between the mean levels of ECP in the respective patient group and of the reference group.

What is claimed is:

1. A method for determining or monitoring a level of activated eosinophils associated with a condition, comprising (a) measuring specifically by an immune assay the level of cytotoxic iso-Eosinophilic Cationic Protein (iso-ECP) in a sample from an individual, wherein the cytotoxicity of the cytotoxic iso-ECP is not inhibited by the monoclonal antibodies EG1 and EG2, and (b) comparing the measured level of the cytotoxic iso-ECP with a predetermined level of the cytotoxic iso-ECP characteristic of the condition to determine or monitor the level of activated eosinophils associated with the condition.

2. The method according to claim 1, wherein the predetermined level of the cytotoxic iso-ECP is a level for healthy individuals.

3. The method according to claim 1, wherein the predetermined level of the cytotoxic iso-ECP is a level measured in a sample taken from the individual at an earlier occasion.

4. The method according to claim 1, wherein the condition is selected from the group consisting of allergic disease, acute asthma, atopic dermatitis, infection, autoimmune conditions in joints, gut, and parasitic disease.

5. The method according to claim 1, wherein the condition is selected from the group consisting of allergic disease and acute asthma.

6. The method according to claim 1, wherein the measuring step comprises contacting the sample from an individual with labeled and unlabeled anti-iso-Eosinophilic Cationic Protein (anti-iso-ECP) antibody, and detecting the level of cytotoxic iso-ECP from a level of complexes formed with the labeled anti-iso-ECP antibody and with the unlabeled anti-iso-ECP antibody, wherein the complexes of cytotoxic iso-ECP and unlabeled anti-iso-ECP are detected with a labeled antibody directed to the unlabeled anti-iso-ECP antibody.

7. The method according to claim 1, wherein the cytotoxic activity of cytotoxic iso-ECP is inhibited by the monoclonal antibody mab 652.

8. The method according to claim 1, wherein the condition is an inflammatory disorder.

9. The method according to claim 1, wherein the condition is an allergic disease.

10. The method according to claim 1, wherein the condition is an asthmatic condition.

11. The method according to claim 1, wherein the measuring step comprises contacting the iso-ECP with labeled or unlabeled anti-iso-Eosinophilic Cationic Protein (anti-iso-ECP) antibody to form an immune complex incorporating the iso-ECP and the labeled or the unlabeled anti-iso-ECP antibody, and detecting the level of complex containing the iso-ECP by either utilizing the signal from the labeled anti-iso-ECP or by contacting the complexes of cytotoxic iso-ECP and unlabeled anti-is-ECP antibody with a labeled antibody directed to the unlabeled anti-iso-ECP antibody, and utilizing the signal from the labeled antibody directed to the unlabeled anti-iso-ECP antibody.

12. A method according to claim 1, wherein the level of cytotoxic iso-Eosinophilic Cationic Protein (iso-ECP) in a sample from an individual is measured by contacting the cytotoxic iso-ECP with a labeled cytotoxic anti-iso-Eosinophilic Cationic Protein (anti-iso-ECP) antibody to form an immune complex incorporating the cytotoxic iso-ECP and the labeled cytotoxic anti-iso-ECP antibody, and detecting the level of complex containing the cytotoxic iso-ECP and the labeled cytotoxic anti-iso-ECP antibody, wherein the cytotoxicity of the cytotoxic iso-ECP is not inhibited by the monoclonal antibodies EG1 and EG2.

13. A cytotoxic anti-iso-Eosinophilic Cationic Protein (anti-iso-ECP) antibody which is specific for a cytotoxic iso-ECP epitope that correlates to cytotoxic activity of cytotoxic iso-ECP.

14. Anti-iso-ECP antibody according to claim 13, wherein the anti-iso-ECP antibody reduces the cytotoxic activity of the cytotoxic iso-ECP to which it specifically binds.

15. Anti-iso-ECP antibody according to claim 13, wherein the anti-iso-ECP antibody reduces the cytotoxic activity of the cytotoxic iso-ECP to which it specifically binds by at least 90%.

16. A method for monitoring a level of activated eosinophils in an individual, comprising (a) measuring specifically by immune assay the level of cytotoxic iso-Eosinophilic Cationic Protein (iso-ECP) in a sample from an individual to be monitored, wherein the cytotoxicity of the cytotoxic iso-ECP is not inhibited by the monoclonal antibodies EG1 and EG2 and (b) comparing the measured level of the cytotoxic iso-ECP with a predetermined level of the cytotoxic iso-ECP for the individual to monitor the level of activated eosinophils in the individual.

17. The method according to claim 16, wherein the cytotoxic activity of cytotoxic iso-ECP is inhibited by the monoclonal antibody mAB 652.

18. The method according to claim 16, wherein the measuring step comprises contacting the sample from an individual to be monitored with labeled and unlabeled anti-iso-Eosinophilic Cationic Protein (anti-iso-ECP) antibody, and detecting the level of cytotoxic iso-ECP from a level of complexes formed with the labeled anti-iso-ECP antibody and with the unlabeled anti-iso-ECP antibody, wherein the complexes of cytotoxic iso-ECP and unlabeled anti-iso-ECP are detected with a labeled antibody directed to the unlabeled anti-iso-ECP antibody.

19. The method according to claim 16, wherein the measuring step comprises contacting the iso-ECP with labeled or unlabeled anti-iso-Eosinophilic Cationic Protein (anti-iso-ECP) antibody to form an immune complex incorporating the iso-ECP and the labeled or the unlabeled anti-iso-ECP antibody, and detecting the level of complex containing the iso-ECP by either utilizing the signal from the labeled anti-iso-ECP or by contacting the complexes of cytotoxic iso-ECP and unlabeled anti-is-ECP antibody with a labeled antibody directed to the unlabeled anti-iso-ECP antibody, and utilizing the signal from the labeled antibody directed to the unlabeled anti-iso-ECP antibody.

20. A method according to claim 16, wherein the level of cytotoxic iso-Eosinophilic Cationic Protein (iso-ECP) in a sample from an individual to be monitored is measured by contacting the cytotoxic iso-ECP with a labeled cytotoxic anti-iso-Eosinophilic Cationic Protein (anti-iso-ECP) antibody to form an immune complex incorporating the cytotoxic iso-ECP and the labeled cytotoxic anti-iso-ECP antibody and detecting the level of complex containing the cytotoxic iso-ECP and the labeled cytotoxic anti-iso-ECP antibody, wherein the cytotoxicity of the cytotoxic iso-ECP is not inhibited by the monoclonal antibodies EG1 and EG2.

* * * * *

UNITED STATES PATENT AND TRADEMARK OFFICE
CERTIFICATE OF CORRECTION

PATENT NO. : 6,733,980 B1
DATED : May 11, 2004
INVENTOR(S) : Per Venge et al.

Page 1 of 1

It is certified that error appears in the above-identified patent and that said Letters Patent is hereby corrected as shown below:

Column 12,
Line 40, change "mab" to -- mAb --.

Column 13,
Line 26, change "mAB" to -- mAb --

Signed and Sealed this

Tenth Day of August, 2004

JON W. DUDAS
*Acting Director of the United States Patent and Trademark Office*